United States Patent
Iaccino et al.

(10) Patent No.: US 10,011,539 B2
(45) Date of Patent: *Jul. 3, 2018

(54) PROCESS FOR CONVERSION OF ACYCLIC $C_5$ COMPOUNDS TO CYCLIC $C_5$ COMPOUNDS AND CATALYST COMPOSITION FOR USE THEREIN

(71) Applicant: ExxonMobil Chemical Patents Inc., Baytown, TX (US)

(72) Inventors: Larry L. Iaccino, Seabrook, TX (US); Jeremy W. Bedard, Houston, TX (US); Wenyih F. Lai, Bridgewater, NJ (US); Robert T. Carr, High Bridge, NJ (US); Jane C. Cheng, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,447

(22) Filed: Oct. 7, 2016

(65) Prior Publication Data

US 2017/0121253 A1 May 4, 2017

Related U.S. Application Data

(60) Provisional application No. 62/250,675, filed on Nov. 4, 2015.

(51) Int. Cl.
| | |
|---|---|
| C07C 5/327 | (2006.01) |
| C07C 5/32 | (2006.01) |
| C07C 5/333 | (2006.01) |
| C07C 5/373 | (2006.01) |
| B01J 29/44 | (2006.01) |

(52) U.S. Cl.
CPC .............. *C07C 5/373* (2013.01); *B01J 29/44* (2013.01); *C07C 2101/10* (2013.01); *C07C 2529/44* (2013.01)

(58) Field of Classification Search
CPC ............ C07C 5/327; C07C 5/32; C07C 5/333
USPC ........................................ 585/365, 366, 369
See application file for complete search history.

(56) References Cited

U.S. PATENT DOCUMENTS

| | | |
|---|---|---|
| 2,438,398 A | 3/1948 | Kennedy et al. |
| 2,438,399 A | 3/1948 | Kennedy et al. |
| 2,438,400 A | 3/1948 | Hetzel et al. |
| 2,438,401 A | 3/1948 | Kennedy et al. |
| 2,438,402 A | 3/1948 | Kennedy et al. |
| 2,438,403 A | 3/1948 | Kennedy et al. |
| 2,438,404 A | 3/1948 | Hetzel et al. |
| 3,631,209 A | 12/1971 | Frech et al. |
| 3,953,368 A | 4/1976 | Sinfelt |
| 4,246,202 A | 1/1981 | Cihonski |
| 4,886,926 A | 12/1989 | Dessau et al. |
| 4,927,525 A | 5/1990 | Chu |
| 5,192,728 A | 3/1993 | Dessau et al. |
| 5,254,787 A | 10/1993 | Dessau |
| 5,283,385 A | 2/1994 | Dessau |
| 5,284,986 A | 2/1994 | Dessau |

FOREIGN PATENT DOCUMENTS

| | | |
|---|---|---|
| DE | 2535809 | 3/1976 |
| WO | WO 89/04818 | 6/1989 |

OTHER PUBLICATIONS

U.S. Appl. No. 62/250,675, filed Nov. 4, 2015, Iaccino et al.
U.S. Appl. No. 62/250,681, filed Nov. 4, 2015, Iaccino et al.
U.S. Appl. No. 62/250,688, filed Nov. 4, 2015, Iaccino et al.
U.S. Appl. No. 62/250,689, filed Nov. 4, 2015, Iaccino et al.
Bricker, J.C. et al., "Advanced Catalytic Dehydrogenation Technologies for Production of Olefins," Topics in Catalysis, 2012, vol. 55, pp. 1309-1314.
Fel'dblyum, V.S., et al. "Cyclization and Dehydrocyclization of $C_5$ Hydrocarbons over Platinum Nanocatalysts and in the Presence of Hydrogen Sulfide," Doklady Chemistry, 2009, vol. 424, Part 2, pp. 27-30.
Kanazirev, V., et al. "Conversion of $C_8$ Aromatics and n-Pentane Over $Ga_2O_3$/HZSM-5 Mechanically Mixed Catalysts," Catalysis Letters, 1991, vol. 9, pp. 35-42.
Kennedy, R.M. et al., "Formation of Cyclopentadiene from 1,3-Pentadiene," Industrial and Engineering Chemistry, 1950, vol. 42, No. 3, pp. 547-552.
Li, X., et al. "Catalytic Dehydroisomerization of n-alkanes to Isoalkenes," Journal of Catalysis, 2008, vol. 255, pp. 134-137.
Lopez, C.M., et al. "n-Pentane Hydroisomerization on Pt Containing HZSM-5, HBEA and SAPO-11," Catalysis Letters, 2008, vol. 122, pp. 267-273.
Marcinkowski, T.E., "Isomerization and Dehydrocyclization of 1,3-Pentadiene," Retrospective Theses and Dissertations, 1979, Paper 433, pp. 1-110.
Vora, B.V., "Development of Dehydrogenation Catalysts and Processes," Topics in Catalysis, 2012, vol. 55, pp. 1297-1308.
Vaezifar, et al. "Dehydrogenation of Isobutane Over Sn/Pt/Na-ZSM-5 Catalysts: The Effect of $SiO_2/Al_2O_3$ Ratio, Amount and Distribution of Pt Nanoparticles on the Catalytic Behavior," Korean J. Chem. Eng., 2011, vol. 28(2), pp. 370-377.
Xinghua, et al. "Aqueous-Phase Catalytic Process for Production of Pentane from Furfural Over Nickel-Based," Fuel, 2010, vol. 89, pp. 2097-2702.
Xu, Y., "Methane activation without using oxidants over Mo/HZSM-5 zeolite catalysts," Catalysis Letters, 1995, vol. 30, pp. 135-149.
Zhang, "Sn-Modified ZSM-5 As Support for Platinum Catalyst in Propane Dehydrogentaion," Industrial & Engineering Chemistry Research, 2011, vol. 50, No. 13, pp. 7896-7902.

*Primary Examiner* — Thuan D Dang (57) ABSTRACT

Disclosed is a process for the conversion of acyclic $C_5$ feedstock to a product comprising cyclic $C_5$ compounds, such as, for example, cyclopentadiene, and catalyst compositions for use in such process. The process comprises the steps of contacting said feedstock and, optionally, hydrogen under acyclic $C_5$ conversion conditions in the presence of a catalyst composition to form said product. The catalyst composition comprising a microporous crystalline aluminosilicate having a constraint index in the range of 3 to 12, a Group 10 metal, and, optionally, a Group 11 metal, in combination with a Group 1 alkali metal and/or a Group 2 alkaline earth metal.

18 Claims, 3 Drawing Sheets

PROCESS FOR CONVERSION OF ACYCLIC $C_5$ COMPOUNDS TO CYCLIC $C_5$ COMPOUNDS AND CATALYST COMPOSITION FOR USE THEREIN

CROSS-REFERENCE TO RELATED APPLICATIONS

This invention claims priority to and the benefit of U.S. Ser. No. 62/250,675, filed Nov. 4, 2015. This application relates to U.S. Ser. No. 62/250,681, filed Nov. 4, 2015, U.S. Ser. No. 62/250,688, filed Nov. 4, 2015, and U.S. Ser. No. 62/250,689, filed Nov. 4, 2015.

FIELD OF THE INVENTION

This invention relates to a process for the conversion of acyclic $C_5$ feedstock to a product comprising cyclic $C_5$ compounds, such as for example, cyclopentadiene, and catalyst compositions for use in such process.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. In addition, cyclopentane and cyclopentene are useful as solvents, and cyclopentene may be used as a monomer to produce polymers and as a starting material for other high value chemicals.

Cyclopentadiene (CPD) is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer products and other high value products could be produced, if additional CPD could be produced, at unconstrained rates and preferably at a cost lower than recovery from steam cracking.

CPD may be produced as the primary product from plentiful $C_5$ feedstock using a catalyst system to produce CPD while minimizing production of light ($C_{4-}$) byproducts. While lower hydrogen content feedstock (for example, cyclics, alkenes, dialkenes) are preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil as well as reduced use in motor fuels due to stringent fuel regulations. $C_5$ feedstock may also be derived from bio-feeds.

Dehydrogenation technologies are currently used to produce mono-olefins and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn or Ca aluminate to dehydrogenate propane. While these processes are successful in dehydrogenating alkanes, they do not perform cyclization which is critical to producing CPD. Pt—Sn/alumina and Pt—Sn/aluminate catalysts exhibit moderate conversion of n-pentane, but such catalyst have poor selectivity and yield to cyclic $C_5$ products.

KX type alumina catalysts (platinum on chlorided alumina) are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. KX type alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al. showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $h^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_{2-5}$ and $C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was the desired product in this process, whereas CPD was an unwanted byproduct. A comparative example was conducted on Pt/Sn-ZSM-5 catalyst at varying temperatures, and is discussed below.

U.S. Pat. No. 2,438,398; U.S. Pat. No. 2,438,399; U.S. Pat. No. 2,438,400; U.S. Pat. No. 2,438,401; U.S. Pat. No. 2,438,402; U.S. Pat. No. 2,438,403; and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over $Pt—Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al. in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites including H-ZSM-5. At intermediate temperatures (250-400° C.), they reported efficient hydroisomerization of n-pentane on the Pt-zeolites with no discussion of cyclopentenes formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

In view of this state of the art, there remains a need for a process to convert acyclic $C_5$ feedstock to non-aromatic, cyclic $C_5$ hydrocarbons, particularly CPD, preferably at commercial rates and conditions. Further, there is a need for a catalytic process targeted for the production of cyclopentadiene which generates cyclopentadiene in high yield from plentiful $C_5$ feedstocks without excessive production of $C_{4-}$ cracked products and with acceptable catalyst aging properties. This invention meets this and other needs.

SUMMARY OF THE INVENTION

In a first aspect, the invention relates to a process for conversion of an acyclic $C_5$ feedstock to a product comprising cyclic $C_5$ compounds. This process comprises the steps of contacting said feedstock and, optionally, hydrogen under acyclic $C_5$ conversion conditions in the presence of a catalyst composition of this invention to form said product.

In a second aspect, the invention relates to a catalyst composition for use in the acyclic $C_5$ conversion process. This catalyst composition comprising a microporous crystalline aluminosilicate comprising a Group 10 metal, optionally a Group 11 metal, in combination with a Group 1 alkali metal and/or a Group 2 alkaline earth metal. The microporous crystalline aluminosilicate has a constraint index in the range of about 3 to about 12, and preferably is selected from the group consisting of ZSM-5, ZSM-11, ZSM-12, ZSM-22, ZSM-23, ZSM-35, ZSM-48, ZSM-50, ZSM-57, ZSM-58, a MCM-22 family material and mixtures of two or more thereof. The Group 10 metal is preferably, platinum, and more preferably in the amount of at least 0.005 wt %, based on the weight of the catalyst composition. The Group 11 metal is preferably copper or silver. The Group 1 alkali metal is preferably sodium.

The microporous crystalline aluminosilicate has a $SiO_2/Al_2O_3$ molar ratio greater than about 25, preferably in the range of from about 50 up to about 1,000.

The catalyst composition has an Alpha Value (as measured prior to the addition of the Group 10 metal, preferably, platinum, and/or prior to the addition of the optional Group 11 metal, preferably, copper or silver) is less than about 25, or in the range of about greater than about 1 to less than about 25.

The Group 11 metal content of said catalyst composition is at least 0.01 molar ratio to the Group 10 metal, based on the molar quantities of each in the catalyst composition.

The molar ratio of said Group 1 alkali metal to Al is at least 0.5, or at least 1, and/or the molar ratio of said Group 2 alkaline earth metal to Al is at least 0.5, or at least 1.

The said catalyst composition provides (i) a conversion of at least about 70% of said acyclic $C_5$ feedstock and/or (ii) a carbon selectivity to cyclic $C_5$ compounds of at least about 30% under acyclic $C_5$ conversion conditions including an n-pentane feedstock with equimolar $H_2$, a temperature in the range of about 550° C. to about 600° C., an n-pentane partial pressure between 3 and 30 psia at the reactor inlet (21 to 207 kPa-a), such as between 3 and 10 psia (21 to 69 kPa-a), and an n-pentane weight hourly space velocity between 10 and 20 $hr^{-1}$.

In a third aspect, the invention relates to a method of making the catalyst composition. The method of making the catalyst composition comprising the steps of:

(a) providing a microporous crystalline aluminosilicate comprising a Group 1 alkali metal and/or a Group 2 alkaline earth metal and a constraint index in the range of about 3 to about 12;

(b) optionally, heating said microporous crystalline aluminosilicate in one or more steps to a first temperature of about 450° C. or above in an atmosphere which comprises an inert gas;

(c) optionally, adding oxygen to said atmosphere until the oxygen concentration in said atmosphere is up to about 20% and then cooling said microporous crystalline aluminosilicate; and (d) contacting said (optionally, cooled) microporous crystalline aluminosilicate of step (a) or (c) with a source of a Group 10 metal, and, optionally, a source of a Group 11 metal, to form said catalyst composition, whereby said catalyst composition having said Group 10 metal, or said optional Group 11 metal, deposited thereon.

In a fourth aspect, the invention relates to a catalyst composition made by any one of the methods of this invention. The amount deposited of said Group 10 metal is at least 0.005 wt %, based on the weight of the catalyst composition. The amount deposited of the optional Group 11 metal is at least 0.01 molar ratio to the Group 10 metal, based on the molar quantities of each in the catalyst composition.

DETAILED DESCRIPTION OF THE INVENTION

Definitions

For the purpose of this specification and appended claims, the following terms are defined.

The term "saturates" includes, but is not limited to, alkanes and cycloalkanes.

The term "non-saturates" includes, but is not limited to, alkenes, dialkenes, alkynes, cyclo-alkenes and cyclo-dialkenes.

The term "cyclic $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene, and xylene, and polynuclear aromatics (PNAs), which include, but are not limited to, naphthalene, anthracene, chrysene, and their alkylated versions. The term "$C_{6+}$ aromatics" includes compounds based upon an aromatic ring having six or more ring atoms, including, but not limited to, benzene, toluene, and xylene and polynuclear aromatics (PNAs) which include, but are not limited to, naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, nickel, palladium, platinum, and a mixture of two or more thereof.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, cesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

The term "constraint index" is defined in U.S. Pat. No. 3,972,832 and U.S. Pat. No. 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types," Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "zeolite" or "microporous crystalline material."

As used herein, the term "carbon selectivity" means the moles of carbon in the respective cyclic $C_5$, CPD, $C_1$, and $C_{2-4}$ formed divided by total moles of carbon in the pentane converted. The term "carbon selectivity to cyclic $C_5$ of at least 30%" means that at least 30 moles of carbon in the cyclic $C_5$ is formed per 100 moles of carbon in the pentane converted.

As used herein, the term "conversion" means the moles of carbon in the acyclic $C_5$ feedstock that is converted to a product. The term "conversion of at least 70% of said acyclic $C_5$ feedstock to a product" means that at least 70% of the moles of said acyclic $C_5$ feedstock was converted to a product.

As used herein, the term "Alpha Value" is used as a measure of the cracking activity of a catalyst and is described in U.S. Pat. No. 3,354,078 and in the Journal of Catalysis, Vol. 4, p. 527 (1965); Vol. 6, p. 278, (1966) and Vol. 61, p. 395, (1980), each incorporated herein by reference. The experimental conditions of the test used herein included a constant temperature of 538° C. and a variable flow rate as described in detail in the Journal of Catalysis, Vol. 61, p. 395, (1980).

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention.

As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes, including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where $U_{mf}$ is minimum fluidizing velocity, $U_{mb}$ is minimum bubbling velocity, $U_c$ is the velocity at which fluctuation in pressure peaks, and tr is transport velocity. These different fluidization regimes have been described in, for example, Kunii, D., Levenspiel, O., Chapter 3 of *Fluidization Engineering, $2^{nd}$* Edition, Butterworth-Heinemann, Boston, 1991 and Walas, S. M., Chapter 6 of *Chemical Process Equipment*, Revised $2^{nd}$ Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$, in at least a portion of the reaction zone, and/or operating at a velocity higher than the minimum fluidization velocity, while maintaining a gradient in gas and/or solid property (such as, temperature, gas, or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering, $2^{nd}$* Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%.

As used herein, the term "cascaded fluid-beds" means a series arrangement of individual fluid-beds such that there can be a gradient in gas and/or solid property (such as, temperature, gas, or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering, $2^{nd}$* Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Revised $2^{nd}$ Edition, Butterworth-Heinemann, Boston, 2010. A fluidized bed reactor, such as a circulating fluidized bed reactor, may be operated as a riser reactor.

As used herein, the term "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow, and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval, and/or a regeneration interval. The duration and/or order of the interval steps may change over time.

As used herein, the term "co-current" refers to a flow of two streams (stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Feedstock

Acyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

The acyclic $C_5$ feedstock useful in the process of this invention comprises pentane, pentene, pentadiene, and mixtures of two or more thereof. Preferably, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ feedstock, optionally, does not comprise $C_6$ aromatic compounds, such as, benzene, preferably $C_6$ aromatic compounds are present at less than 5 wt %, preferably less than 1 wt %, preferably present at less than 0.01 wt %, preferably at 0 wt %.

The acyclic $C_5$ feedstock, optionally, does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic $C_5$ feedstock, optionally, does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock optionally does not comprise $C_{4-}$ compounds, any $C_{4-}$ compounds are present at less than 5 wt %, preferably less than 1 wt %, preferably present at less than 0.01 wt %, preferably at 0 wt %.

Acyclic $C_5$ Conversion Process

The first aspect of the invention is a process for conversion of an acyclic $C_5$ feedstock to a product comprising cyclic $C_5$ compounds. The process comprises the steps of contacting said feedstock and, optionally, hydrogen under acyclic $C_5$ conversion conditions in the presence of any one of the catalyst compositions of this invention to form said product. The catalyst composition comprises a microporous crystalline aluminosilicate having a constraint index in the range of about 3 to about 12, a Group 10 metal, optionally, a Group 11 metal, in combination with a Group 1 alkali metal and/or a Group 2 alkaline earth metal.

The first aspect of the invention is also a process for conversion of an acyclic $C_5$ feedstock to a product comprising cyclic $C_5$ compounds, the process comprising the steps of contacting said feedstock and, optionally, hydrogen under acyclic $C_5$ conversion conditions in the presence of any one of the catalyst compositions made by any one of the methods of this invention to form said product.

The acyclic $C_5$ conversion process can be conducted in a wide range of reactor configurations including: convectively heated tubes (as described in U.S. Ser. No. 62/250,674, filed Nov. 4, 2015), fired tubes (as described in U.S. Ser. No. 62/250,693, filed Nov. 4, 2015), a riser reactor (as described in U.S. Ser. No. 62/250,682, filed Nov. 4, 2015), a circulating fluidized bed or a circulating settling bed with counter-current flow (as described in U.S. Ser. No. 62/250,680, filed Nov. 4, 2015), and a cyclic fluidized bed reactor or a cyclic fixed bed reactor (as described in U.S. Ser. No. 62/250,677, filed Nov. 4, 2015). In addition, the $C_5$ conversion process can be conducted in a single reaction zone or in a plurality of reaction zones, such as an adiabatic reaction zone followed by a diabatic reaction zone (as described in U.S. Ser. No. 62/250,697, filed Nov. 4, 2015).

Typically, the acyclic $C_5$ hydrocarbon(s) contained in the $C_5$ feedstock is fed into a first reactor loaded with a catalyst, where the acyclic $C_5$ hydrocarbons contact the catalyst under conversion conditions, whereupon at least a portion of the acyclic $C_5$ hydrocarbon(s) molecules are converted into CPD molecules, and a reaction product containing CPD and, optionally, other cyclic hydrocarbons (e.g., $C_5$ cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as $C_1$-$C_4$ hydrocarbons, is also fed into the first reactor (as described in U.S. Ser. No. 62/250,702, filed Nov. 4, 2015). Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles.

The product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. The cyclic $C_5$ compounds comprise at least about 20 wt %, or 30 wt %, or 40 wt %, or 50 wt % cyclopentadiene, or in the range of from about 10 wt % to about 80 wt %, alternately 20 wt % to 70 wt % of cyclopentadiene.

The acyclic $C_5$ conversion conditions include at least a temperature, a partial pressure, and a weight hourly space velocity (WHSV). The temperature is in the range of about 400° C. to 700° C., or about 450° C. to about 800° C., or in the range from about 500° C. to about 650° C., preferably, in the range from about 500° C. to about 600° C.

The partial pressure is in the range of about 3 psia to about 100 psia at the reactor inlet (21 to 689 kPa-a), or in the range from about 3 psia to about 50 psia (21 to 345 kPa-a), preferably, in the range from about 3 psia to about 20 psia (21 to 138 kPa-a). The weight hourly space velocity is in the range from about 1 hr$^{-1}$ to about 50 hr$^{-1}$, or in the range from about 1 hr$^{-1}$ to about 20 hr$^{-1}$. Such conditions include a molar ratio of the optional hydrogen co-feed to the acyclic $C_5$ hydrocarbon in the range of about 0 to 3 (e.g., 0.01 to 3.0), or in the range from about 0.5 to about 2. Such conditions may also include co-feed $C_1$-$C_4$ hydrocarbons with the acyclic $C_5$ feed.

In any embodiment, this invention relates to a process for conversion of n-pentane to cyclopentadiene comprising the steps of contacting n-pentane and, optionally, hydrogen (if present, typically $H_2$ is present at a molar ratio of hydrogen to n-pentane of 0.01 to 3.0) with one or more catalyst compositions, including but not limited to the catalyst compositions described herein, to form cyclopentadiene at a temperature of 400° C. to 700° C., a partial pressure of 3 psia to about 100 psia at the reactor inlet (21 to 689 kPa-a), and a weight hourly space velocity of 1 hr$^{-1}$ to about 50 hr$^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction steps are not shown) is:

n-pentaneCPD+3$H_2$.

Additional overall reactions include, but are not limited to:

n-pentane1,3-pentadiene+2$H_2$,
n-pentane1-pentene+$H_2$,
n-pentane→2-pentene+$H_2$,
n-pentane→2-methyl-2-butene+$H_2$,
n-pentane→cyclopentane+$H_2$,
cyclopentane→cyclopentene+$H_2$, or
cyclopentene→CPD+$H_2$.

Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; $C_8$, $C_7$, and $C_6$ hydrocarbons such as one-ring aromatics; CPD (the desired product); unreacted $C_5$ feedstock material such as n-pentane; $C_5$ by-products such as pentenes (1-pentene, 2-pentene, e.g.), pentadienes (1,3-pentadiene; 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like; $C_4$ by-products such as butane, 1-butene, 2-butene, 1,3-butadiene, 2-methylpropane, 2-methyl-1-propene, and the like; $C_3$ by-products such as propane, propene, and the like; $C_2$ by-products such as ethane and ethene, methane, and hydrogen.

The first reactor hydrocarbon effluent may comprise CPD at a concentration of C(CPD)1 wt %, based on the total weight of the $C_5$ hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80, or 85 as long as a1<a2.

The first reactor hydrocarbon effluent may comprise acyclic diolefins at a total concentration of C(ADO)1 wt %, based on the total weight of the $C_5$ hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1<b2. Preferably, 0.5≤C(ADO)≤10.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic $C_5$ hydrocarbons to CPD and hydrogen results in substantial volume increase (assuming constant total system pressure), a low partial pressure of CPD and/or a low partial pressure of hydrogen in the reaction mixture favors the conversion of acyclic $C_5$ hydrocarbons. The total partial pressure of $C_5$ hydrocarbons and hydrogen in the first reactor effluent at the outlet is desired to be lower than atmospheric pressure. Thus, where insufficient co-feedstock of a $C_1$-$C_4$ hydrocarbon or other co-feedstock is introduced into the first reactor, the total overall pressure of the first reactor effluent is desirably sub-atmospheric, in order to achieve a level of satisfactory conversion from acyclic $C_5$ hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, can be used for that purpose (as described in U.S. Ser. No. 62/250,708, filed Nov. 4, 2015).

Catalyst Composition

The second aspect of the invention is a catalyst composition for the conversion of an acyclic $C_5$ feedstock and, optionally, hydrogen to a product comprising cyclic $C_5$ compounds including cyclopentadiene. The catalyst composition comprises a microporous crystalline aluminosilicate, a Group 10 metal, and, optionally, a Group 11 metal, in combination with a Group 1 alkali metal and/or a Group 2 alkaline earth metal.

The microporous crystalline aluminosilicate has a constraint index in the range of about 3 to about 12. Suitable aluminosilicates having a constraint index of 3 to 12 include and are selected from the group consisting of ZSM-5, ZSM-11, ZSM-22, ZSM-23, ZSM-35, ZSM-48, ZSM-50, ZSM-57, ZSM-58, a MCM-22 family material, and mixtures of two or more thereof. Preferably, the microporous crystalline aluminosilicate that has a constraint index in the range of about 3 to about 12 is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-50 is described in U.S. Pat. No. 4,640,829. ZSM-57 is described in U.S. Pat. No. 4,873,067. ZSM-58 is described in U.S. Pat. No. 4,698,217. Constraint index and a method for its determination are described in U.S. Pat. No. 4,016,218, referenced above. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0293032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

The microporous crystalline aluminosilicate has a $SiO_2/Al_2O_3$ molar ratio greater than about 25, or greater than about 50, or greater than about 100, or greater than about 400, or in the range from about 100 to about 400, or from about 100 to about 500, or from about 50 to about 1000.

The Group 10 metal includes, or is selected from the group consisting of nickel, palladium, and platinum, preferably platinum. The Group 10 metal content of said catalyst composition is at least 0.005 wt %, based on the weight of the catalyst composition. The Group 10 content is in the range from about 0.005 wt % to about 10 wt %, or from about 0.005 wt % up to about 1.5 wt %, based on the weight of the catalyst composition.

The Group 1 alkali metal includes, or is selected from the group consisting of lithium, sodium, potassium, rubidium, cesium, and mixtures of two or more thereof, preferably sodium.

The Group 2 alkaline earth metal, includes, or is selected from the group consisting of beryllium, magnesium, calcium, strontium, barium, and mixtures of two or more thereof.

The Group 11 metal is selected from the group consisting of copper, silver, gold, and mixtures of two or more thereof; preferably copper or silver.

The Group 11 metal content of the catalyst composition is such that the molar ratio of Group 11 metal to Group 10 metal is at least 0.01, based on the molar quantities of each in the catalyst composition. Preferably, the molar ratio of Group 11 metal to Group 10 metal is in the range from about 0.1 to 10 or from about 0.5 to 5 based on the molar quantities of each in the catalyst composition. The Group 11 metal may be added to the catalyst composition during or after synthesis of the microporous crystalline molecular sieve as any suitable Group 11 metal compound.

The catalyst composition has an Alpha Value (as measured prior to the addition of the Group 10 metal, preferably platinum, and/or prior to the addition of the optional Group 11 metal, preferably, copper or silver) is less than about 25, or in the range of greater than about 1 to less than about 25, preferably, less than about 15, or in the range of greater than about 1 to less than about 15.

The molar ratio of said Group 1 alkali metal to Al is at least about 0.5, or at least about 1, or from at least about 1 up to about 3, preferably at least about 2, more preferably at least about 3.

The molar ratio of said Group 2 alkaline earth metal to Al is at least about 0.5, or at least about 1, or from at least about 1 up to about 3, preferably at least about 2, more preferably at least about 3.

The metal is present as an oxide. The Group 1 alkali metal is present as an oxide and the metal is selected from the group consisting of lithium, sodium, potassium, rubidium, cesium, and mixtures of two or more thereof. The Group 2 alkaline earth metal is present as an oxide and the metal is selected from the group consisting of beryllium, magnesium, calcium, strontium, barium, and mixtures of two or more thereof.

The use of the catalyst compositions of this invention provides a conversion of at least about 70%, or at least about 75%, or at least about 80%, or in the range from about 60% to about 80%, of said acyclic $C_5$ feedstock under acyclic $C_5$ conversion conditions of an n-pentane containing feedstock with equimolar $H_2$, a temperature in the range of about 550° C. to about 600° C., an n-pentane partial pressure between 3 and 10 psia (21 to 69 kPa-a), and an n-pentane weight hourly space velocity between 10 and 20 $hr^{-1}$.

The use of any one of the catalyst compositions of this invention provides a carbon selectivity to cyclic $C_5$ compounds of at least about 30%, or at least about 40%, or at least about 50%, or in the range from about 30% to about 50%, under acyclic $C_5$ conversion conditions, including an n-pentane feedstock with equimolar $H_2$, a temperature in the range of about 550° C. to about 600° C., an n-pentane partial pressure between 3 psia and 10 psia (21 to 69 kPa-a), and an n-pentane weight hourly space velocity between 5 $hr^{-1}$ and 20 $hr^{-1}$, such as between 10 $hr^{-1}$ and 20 $hr^{-1}$.

The use of any one of the catalyst compositions of this invention provides a carbon selectivity to cyclopentadiene of at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure between 3 psia and 30 psia at the reactor inlet (21 to 207 kPa-a), such as between 3 psia and 10 psia (21 to 69 kPa-a), and an n-pentane weight hourly space velocity between 5 $hr^{-1}$ and 20 $hr^{-1}$, such as between, 10 $hr^{-1}$ and 20 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 wt % to 99 wt % of the materials of the invention based on the combined weight of the matrix (binder) and material of the invention. The relative proportions of microporous crystalline material and matrix may vary widely, with the crystal content ranging from about 1 wt % to about 90 wt % and more usually, particularly when the composite is prepared in the form of beads, in the range of about 2 wt % to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Method of Making the Catalyst Compositions

In the third aspect of the invention, the method of making the catalyst composition comprising the steps of:
(a) providing a microporous crystalline aluminosilicate comprising a Group 1 alkali metal and/or a Group 2 alkaline earth metal and a constraint index in the range of about 3 to about 12, preferably such microporous crystalline aluminosilicate of this invention;
(b) optionally, heating said microporous crystalline aluminosilicate in one or more steps to a first temperature of at least about 450° C., or 500° C., or 550° C. in an atmosphere which comprises an inert gas, preferably nitrogen;
(c) optionally, adding oxygen to said atmosphere until the oxygen concentration in said atmosphere is up to about 10%, or about 20%, or about 30% and then cooling said microporous crystalline aluminosilicate, preferably cooling to about ambient temperature, for example, about 25° C.; and
(d) contacting said (optionally, cooled) microporous crystalline aluminosilicate of step (a) or (c) with a source of a Group 10 metal, preferably platinum, and/or optionally a source of a Group 11 metal, preferably copper or silver, to form said catalyst composition, whereby said catalyst composition having said Group 10 metal, and/or optionally said Group 11 metal, deposited thereon.

The Group 10 metal and/or the optional Group 11 metal may be added to the catalyst composition during or after synthesis of the crystalline molecular sieve as any suitable Group 10 metal compound.

One Group 10 metal is platinum, and a source of platinum includes, but is not limited to, one or more platinum salts, such as, for example, platinum nitrate, chloroplatinic acid, platinous chloride, platinum amine compounds, particularly, tetraamine platinum hydroxide, and mixtures of two or more thereof. Alternatively, a source of platinum is selected from the group consisting of chloroplatinic acid, platinous chloride, platinum amine compounds, particularly, tetraamine platinum hydroxide, and mixtures of two or more thereof.

The source of optional Group 11 metal is a source of copper or silver. The source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof. The source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof.

When Group 10 and/or optional Group 11 metals are added post-synthesis, they may be added by incipient wetness, spray application, solution exchange, and chemical vapor disposition, or by other means known in the art.

The amount deposited of said Group 10 metal is at least 0.005 wt %, based on the weight of the catalyst composition, or in the range from 0.005 wt % to 10 wt %, or from about 0.005 wt % up to about 1.5 wt %, based on the weight of the catalyst composition.

The Group 11 metal content of said catalyst composition is at least 0.01 molar ratio to the Group 10 metal, based on the molar quantities of each in the catalyst composition. The Group 11 molar ratio to Group 10 metal is in the range from about 0.1 to 10 or from about 0.5 to 5 based on the molar quantities of each in the catalyst composition.

In the fourth aspect of the invention, the catalyst composition is made by the method of this invention.

INDUSTRIAL APPLICABILITY

The first hydrocarbon reactor effluent obtained during the acyclic $C_5$ conversion process containing cyclic, branched, and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

Diels-Alder reaction product where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the mono-olefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

norbornene   ethylidene norbornene tetracyclododecene   norbornadiene oxygen substituted norbornene

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

ROMP catalyst

Separated cyclopentane is useful as a blowing agent and as a solvent. Linear and branched $C_5$ products are useful for conversion to higher olefins and alcohols. Cyclic and non-cyclic $C_5$ products, optionally after hydrogenation, are useful as octane enhancers and transportation fuel blend components.

The following examples illustrate the present invention. Numerous modifications and variations are possible and it is to be understood that within the scope of the appended claims, the invention may be practiced otherwise than as specifically described herein.

EXAMPLES

Measurement of Total Surface Area by BET

The total BET was measured by nitrogen adsorption/desorption with a Micromeritics Tristar II 3020 instrument after degassing of the calcined zeolite powders for 4 hrs at 350° C. More information regarding the method can be found, for example, in "Characterization of Porous Solids and Powders: Surface Area, Pore Size and Density", S. Lowell et al., Springer, 2004.

X-Ray Diffraction Patterns

The X-ray diffraction data (powder XRD or XRD) were collected with a Bruker D4 Endeavor diffraction system with a VÅNTEC multichannel detector using copper K-alpha radiation. The diffraction data were recorded by scanning mode with 0.018 degrees two-theta, where theta is the Bragg angle, and using an effective counting time of about 30 seconds for each step.

Comparative Example—Pt/Sn-ZSM-5 Catalyst Synthesis and Performance Evaluation

Experiments were conducted on the conversion of n-pentane over Pt/Sn-ZSM-5 catalyst prepared in accordance with the general procedures described in U.S. Pat. No. 5,284,986 and selectivity/yield of cyclic $C_5$, $C_1$, and $C_{2-4}$ cracking products, at 451° C. (average values over 1 hour at each temperature) for a catalyst composition of 0.5 g ZSM-5 (747:1 $SiO_2$:$Al_2O_3$)/2.0 wt % Sn/0.9 wt % Pt, at conditions of 6.9 psia (48 kPa-a) for n-pentane ($C_5H_{12}$), 1:1 molar $H_2$:$C_5$, 2.4 WHSV, 50 psia total (345 kPa-a). Data is shown for performance of the catalyst fresh and after a 5 hour treatment in $H_2$ at 650° C. In Table 1A, the selectivities and yields are expressed on a molar percentage basis for the respective cyclic $C_5$, CPD, $C_1$, and $C_{2-4}$ of hydrocarbons formed; i.e., the molar selectivity is the moles of the respective cyclic $C_5$, CPD, $C_1$, and $C_{2-4}$ formed divided by total moles of pentane converted. In Table 1B, the selectivities and yields are expressed on a carbon percentage basis for the respective cyclic $C_5$, CPD, $C_1$, and $C_{2-4}$ of hydrocarbons formed; i.e., the carbon selectivity is the moles carbon in the respective cyclic $C_5$, CPD, $C_1$, and $C_{2-4}$ formed divided by total moles of carbon in the pentane converted.

As can be seen, Table 1A and Table 1B show moderate, 36%, conversion of n-pentane with 23% molar selectivity to cyclic $C_5$ species on a fresh catalyst composition. The selectivity to cyclic products greatly reduced after $H_2$ treatment at 650° C., demonstrating undesired catalyst aging.

TABLE 1A

| Temperature (° C.) | Conversion (%) $C_5H_{12}$ | Selectivity (mol %) | | | Yield (mol %) | | |
|---|---|---|---|---|---|---|---|
| | | $cC_5$ | $C_1$ | $C_{2-4}$ | $cC_5$ | $C_1$ | $C_{2-4}$ |
| 451 | 36 | 23 | 1.5 | 12 | 8.5 | 0.5 | 4.4 |
| 452, Post $H_2$ | 30 | 7.7 | 0.4 | 7.2 | 2.3 | 0.1 | 2.1 |

TABLE 1B

| Temperature | Conversion (%) | Selectivity (C %) | | | Yield (C %) | | |
|---|---|---|---|---|---|---|---|
| (° C.) | $C_5H_{12}$ | $cC_5$ | $C_1$ | $C_{2-4}$ | $cC_5$ | $C_1$ | $C_{2-4}$ |
| 451 | 36 | 25.3 | 0.3 | 7.5 | 9.2 | 0.1 | 2.7 |
| 452, Post $H_2$ | 30 | 7.6 | 0.1 | 4.0 | 2.2 | 0.0 | 1.2 |

Example 1—ZSM-5 Catalyst Composition Synthesis

A synthesis mixture with ~20.3% solids was prepared from 10,000 g of deionized (DI) water, 600 g of 50% NaOH solution, 25 g of 45% Sodium Aluminate solution, 730 g of n-propyl amine 100% solution, 80 g of ZSM-5 seed crystals, and 3,190 g of Ultrasil PM™ Modified silica. These components were mixed in a 5-gal pail container and then charged into a 5-gal autoclave after mixing. The synthesis mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

Figure 1:
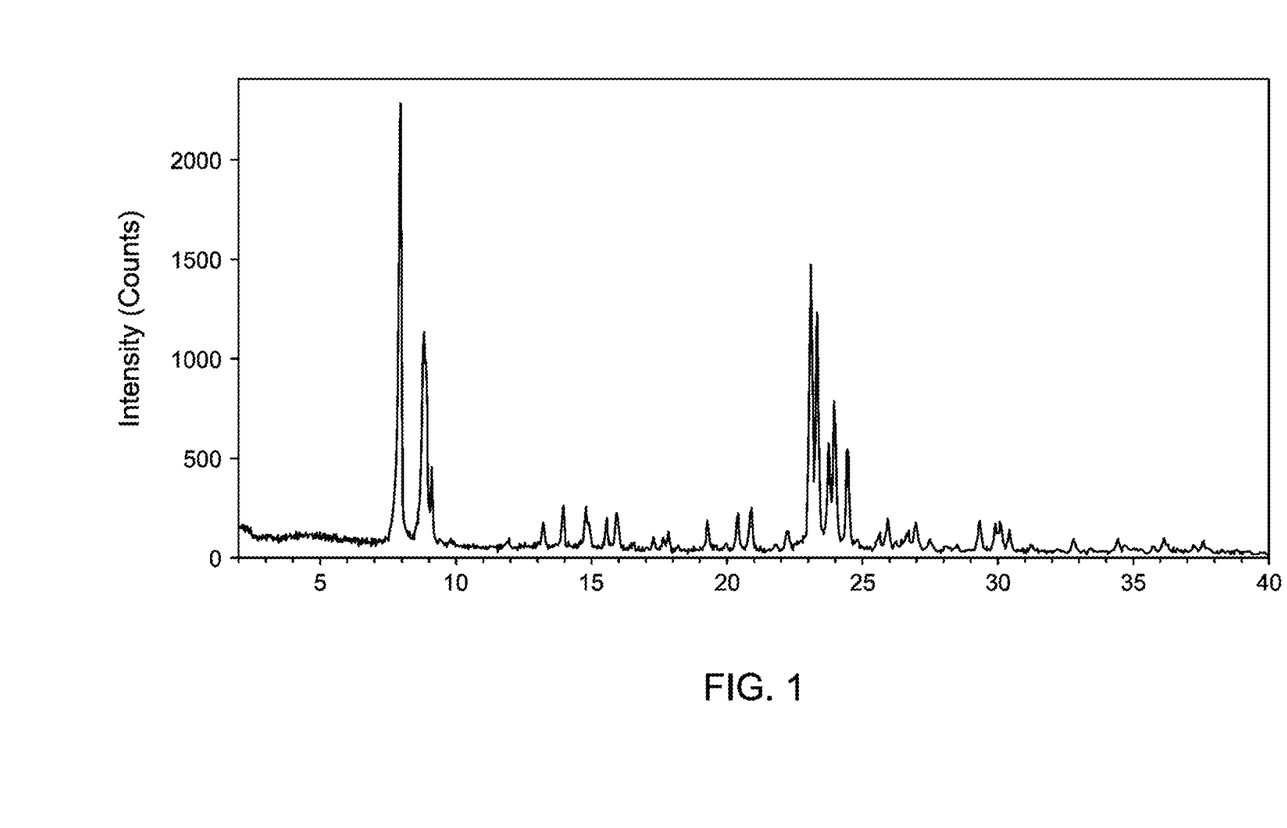
FIG. 1 shows an X-ray diffraction (XRD) pattern of the as-synthesized material produced in Example 1.
Figure 2:
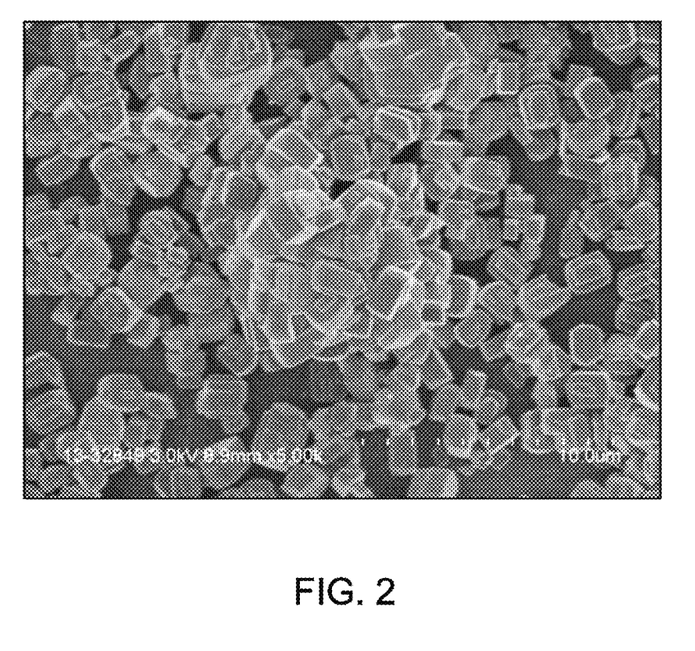
FIG. 2 shows a scanning electron microscope (SEM) image of the as-synthesized material produced in Example 1.

The synthesis mixture was mixed and reacted at 230° F. (110° C.) at 250 rpm for 72 hours. The resulting product was filtered and washed with DI water and then dried in the oven at ~250° F. (121° C.) overnight. The XRD pattern of the as-synthesized material shows the typical pure phase of ZSM-5 topology as shown in FIG. 1. The SEM shown in FIG. 2 is of the as-synthesized material showing that the material was composed of a mixture of large crystals with a size of ~2 micron. A portion of the as-synthesized crystals were converted (for characterization) into the hydrogen form by three ion exchanges with ammonium nitrate solution at room temperature, followed by drying at 250° F. (121° C.) and calcination at 1000° F. (540° C.) for 6 hours. The resulting ZSM-5 crystals had a $SiO_2/Al_2O_3$ molar ratio of ~414, total surface area (SA)/(micropore SA+mesopore SA) of 490 (440+51) m²/g, Hexane sorption of 117 mg/g and an Alpha value (as measured on the proton form) of 31. A second portion of the material was used as synthesized for Pt impregnation.

ZSM-5, having a $SiO_2/Al_2O_3$ molar ratio of 414 and a sodium content of 0.38 wt %, was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 0.5 wt % Pt was added via incipient wetness impregnation using an aqueous solution of tetraamine platinum hydroxide. The catalyst composition was dried in air at room temperature for 2 hours, then at 250° F. (121° C.) for 4 hours, and lastly calcined in air at 660° F. (349° C.) for 3 hours. The catalyst composition powder was pressed (15 ton), crushed, and sieved to obtain 20-40 mesh particle size.

Example 2—Catalyst Composition Performance Evaluation

The above material of Example 1 was evaluated for performance. The catalyst composition (0.5 g) was physically mixed with quartz (1.5 g, 60-80 mesh) and loaded into a reactor. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested for performance with feed of n-pentane, $H_2$, and balance He, typically at 550° C.-600° C., 5.0 psia (35 kPa-a) $C_5H_{12}$, 1.0 molar $H_2:C_5H_{12}$, 14.7 h$^{-1}$ WHSV, and 30 psig (207 kPa) total. Catalyst composition stability and regenerability was tested post initial tests at 550° C. to 600° C. by treatment with $H_2$ (200 mL/min, 30 psig (207 kPa), 650° C.) for 5 hours, then retesting performance at 600° C.

Example 3—ZSM-5 Catalyst Composition Synthesis—Lower Sodium

A synthesis mixture with ~20.3% solids was prepared from 10,000 g of deionized (DI) water, 600 g of 50% NaOH solution, 25 g of 45% Sodium Aluminate solution, 730 g of n-propyl amine 100% solution, 80 g of ZSM-5 seed crystals, and 3,190 g of Ultrasil PM™ Modified silica. These components were mixed in a 5-gal pail container and then charged into a 5-gal autoclave after mixing. The synthesis mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

The synthesis mixture was mixed and reacted at 230° F. (110° C.) at 250 rpm for 72 hours. The resulting product was filtered and washed with DI water and then dried in the oven at ~250° F. (121° C.) overnight. The XRD pattern of the as-synthesized material shows the typical pure phase of ZSM-5 topology as shown in FIG. 1. The SEM shown in FIG. 2 is of the as-synthesized material showing that the material was composed of a mixture of large crystals with a size of ~2 micron. A portion of the as-synthesized crystals were converted (for characterization) into the hydrogen form by three ion exchanges with ammonium nitrate solution at room temperature, followed by drying at 250° F. (121° C.) and calcination at 1000° F. (540° C.) for 6 hours. The resulting ZSM-5 crystals had a $SiO_2/Al_2O_3$ molar ratio of ~414, total surface area (SA)/(micropore SA+mesopore SA) of 490 (440+51) m²/g, Hexane sorption of 117 mg/g and an Alpha value (as measured on the proton form) of 31. A second portion of the material was used as synthesized for Pt impregnation.

ZSM-5 having a $SiO_2/Al_2O_3$ molar ratio of 414 and a sodium content of 0.20 wt % and 0.02 wt % was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 0.5 wt % Pt was added via incipient wetness impregnation using an aqueous solution of tetraamine platinum hydroxide. The catalyst composition was dried in air at room temperature for 2 hours, then at 250° F. (121° C.) for 4 hours, and lastly calcined in air at 660 F (349° C.) for 3 hours. The catalyst composition powder was pressed (15 ton), crushed, and sieved to obtain 20-40 mesh particle size.

Example 4—Catalyst Composition Performance Evaluation

The above material of Example 3 was evaluated for performance. The catalyst composition (0.5 g) was physically mixed with quartz (1.5 g, 60-80 mesh) and loaded into a reactor. The catalyst composition was dried for 1 hour under He (100 mL/min, 30 psig (207 kPa), 250° C.) then reduced for 1 hour under $H_2$ (200 mL/min, 30 psig (207 kPa), 500° C.). The catalyst composition was then tested for performance with feed of n-pentane, $H_2$, and balance He, typically at 550-600° C., 5.0 psia (35 kPa-a) $C_5H_{12}$, 1.0 molar $H_2:C_5H_{12}$, 14.7 hr$^{-1}$ WHSV, and 30 psig (207 kPa) total. Catalyst composition stability and regenerability was tested post initial tests at 550 to 600° C. by treatment with $H_2$ (200 mL/min, 30 psig (207 kPa), 650° C.) for 5 hrs then retesting performance at 600° C.

Cyclopentadiene and three equivalents of hydrogen are produced by dehydrogenation and cyclization of n-pentane (Equation 1). This is achieved by flowing n-pentane over a solid-state, Pt containing catalyst composition at elevated temperature. The performance of ZSM-5(414:1)/0.5% Pt of Example 3 was evaluated based on n-pentane conversion, cyclic $C_5$ production ($cC_5$), cracking yields, and stability. These results are summarized in Table 2A and Table 2A iC5, Table 2b and 2B iC5, and FIG. 3A and FIG. 3B.

Equation (1)

TABLE 2A

| Temperature | Conversion (%) | Selectivity (mol %) | | | | | Yield (mol %) | | | | | |
|---|---|---|---|---|---|---|---|---|---|---|---|---|
| (° C.) | C5H12 | cC5 | CPD | C1 | C2-4 | iC5 | cC5 | CPD | C1 | C2-4 | iC5 | cC5:C1-4 |
| 545 | 71 | 33 | 20 | 11 | 21 | 4.4 | 24 | 14 | 8.1 | 15 | 3.1 | 1.0 |
| 570 | 80 | 37 | 26 | 13 | 22 | 3.7 | 30 | 21 | 10 | 17 | 3.0 | 1.1 |
| 595 | 84 | 40 | 32 | 13 | 22 | 3.1 | 34 | 26 | 11 | 18 | 2.6 | 1.1 |
| 595, Post H2 | 76 | 38 | 30 | 16 | 22 | 2.4 | 29 | 23 | 12 | 17 | 1.8 | 1.0 |

TABLE 2A iC5

| Temperature | Conversion (%) | Selectivity (mol %) | | | | Yield (mol %) | | | |
|---|---|---|---|---|---|---|---|---|---|
| (° C.) | C5H12 | iC5 | iC5o | iC5= | iC5== | iC5 | iC5o | iC5= | iC5== |
| 545 | 71 | 4.4 | 1.1 | 3.2 | 0.04 | 3.1 | 0.8 | 2.3 | 0.03 |
| 570 | 80 | 3.7 | 0.8 | 2.8 | 0.05 | 3.0 | 0.7 | 2.3 | 0.04 |
| 595 | 84 | 3.1 | 0.7 | 2.4 | 0.05 | 2.6 | 0.6 | 2.0 | 0.05 |
| 595, Post H2 | 76 | 2.4 | 0.6 | 1.8 | 0.04 | 1.8 | 0.5 | 1.4 | 0.03 |

TABLE 2B

| Temperature | Conversion (%) | Selectivity (C %) | | | | | Yield (C %) | | | | | |
|---|---|---|---|---|---|---|---|---|---|---|---|---|
| (° C.) | C5H12 | cC5 | CPD | C1 | C2-4 | iC5 | cC5 | CPD | C1 | C2-4 | iC5 | cC5:C1-4 |
| 545 | 71 | 40 | 24 | 2.8 | 15 | 5.3 | 28 | 17 | 2.0 | 11 | 3.7 | 2.2 |
| 570 | 80 | 45 | 32 | 3.1 | 16 | 4.5 | 36 | 26 | 2.5 | 13 | 3.6 | 2.3 |
| 595 | 84 | 50 | 39 | 3.3 | 16 | 3.8 | 42 | 33 | 2.8 | 14 | 3.2 | 2.5 |
| 595, Post H2 | 76 | 48 | 38 | 4.1 | 17 | 3.0 | 37 | 29 | 3.1 | 13 | 2.3 | 2.3 |

TABLE 2B iC5

| Temperature | Conversion (%) | Selectivity (C %) | | | | Yield (C %) | | | |
|---|---|---|---|---|---|---|---|---|---|
| (° C.) | C5H12 | iC5 | iC5o | iC5= | iC5== | iC5 | iC5o | iC5= | iC5== |
| 545 | 71 | 5.3 | 1.4 | 3.8 | 0.05 | 3.7 | 1.0 | 2.7 | 0.04 |
| 570 | 80 | 4.5 | 1.0 | 3.5 | 0.06 | 3.6 | 0.8 | 2.8 | 0.04 |
| 595 | 84 | 3.8 | 0.8 | 2.9 | 0.07 | 3.2 | 0.7 | 2.5 | 0.06 |
| 595, Post H2 | 76 | 3.0 | 0.8 | 2.2 | 0.05 | 2.3 | 0.6 | 1.7 | 0.03 |

Table 2A and Table 2B show the conversion of n-pentane and selectivity and yield of cyclic $C_5$, CPD, iso-$C_5$, $C_1$, and $C_{2-4}$ cracking products at varying temperatures (average values over 8 hours at each temperature) for a catalyst composition of 0.5 g ZSM-5(Si:$Al_2$ molar ratio 414:1)/0.5 wt % Pt at conditions of 5.0 psia (35 kPa-a) $C_5H_{12}$, 1:1 molar $H_2$:$C_5$, 14.7 WHSV, 45 psia (310 kPa-a) total. In Table 2A, the selectivities and yields are expressed on a molar percentage basis for the respective cyclic $C_5$, CPD, iso-$C_5$, $C_1$, and $C_{2-4}$ of hydrocarbons formed; i.e., the molar selectivity is the moles of the respective cyclic $C_5$, CPD, $C_1$, and $C_{2-4}$ formed divided by total moles of pentane converted. In Table 2B, the selectivities and yields are expressed on a carbon percentage basis for the respective cyclic $C_5$, CPD, iso-$C_5$, $C_1$, and $C_{2-4}$ of hydrocarbons formed; i.e., the carbon selectivity is the moles carbon in the respective cyclic $C_5$, CPD, iso-$C_5$, $C_1$, and $C_{2-4}$ formed divided by total moles of carbon in the pentane converted.

Figure 3A:
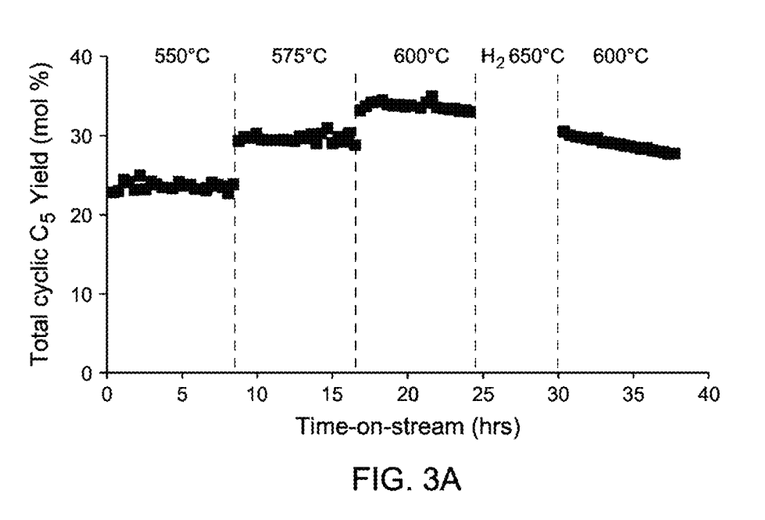
FIGS. 3A and 3B show the yield of cyclic $C_5$ at varying temperatures before and after hydrogen treatment resulting from the catalyst composition performance evaluation of Example 4.
Figure 3B:
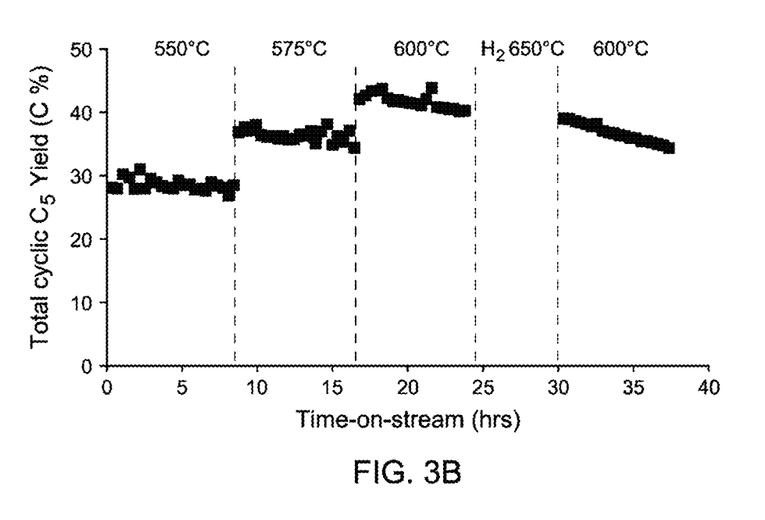

As can be seen, Table 2A and Table 2B show greater than 80% conversion of pentane, at high WHSV, and 40% selectivity to cyclic $C_5$ species at 595° C. While not the specific end product, cyclopentane and cyclopentene can be recycled to produce CPD. FIGS. 3A and 3B show this activity is maintained for 8 hours at each temperature, and after 5 hours of $H_2$ treatment at 650° C. This performance is greatly superior to other dehydrogenation catalyst compositions, aluminas, and aluminates, as discussed above.

Tables 2A iC5 and 2B iC5 further specify the individual iC5 components which are shown as totals in Tables 2A and 2B. iC5o is iso pentane; including 2-methyl butane and 3-methyl butane. iC5= is isopentenes including 2-methyl butene and 3-methyl butene. iC5≡ is iso-pentadienes; including 2-methyl butadiene and 3-methyl butadiene. These results show the low levels of iso-pentadienes that are possible with the present invention.

In an additional comparison, a catalyst composition of ZSM-5(Si:$Al_2$ molar ratio 414:1)/0.5 wt % Pt of Example 3 also produces in Example 4 the $C_1$ and $C_{2-4}$ cracking products as lower value, undesired side products that cannot be recycled in this process, but can be separated and used as feedstock for other processes or as fuels.

g ZSM-5 (Si:$Al_2$ molar ratio 414)/1.0% Pt, 5.0 psia (35 kPa-a) $C_5H_{12}$, 1:1 molar $H_2$:$C_5$, 14.7 WHSV, 45 psia total (310 kPa-a). In Table 3A, the sodium content is 0.20 wt % based on weight of the catalyst composition. In Table 3B, the sodium content is 0.02 wt % based on weight of the catalyst composition. In these Tables, the selectivities and yields are expressed on a carbon percentage basis for the respective cyclic $C_5$, CPD, $C_1$, and $C_{2-4}$ of hydrocarbons formed; i.e., the carbon selectivity is the moles carbon in the respective cyclic $C_5$, CPD, $C_1$, and $C_{2-4}$ formed divided by total moles of carbon in the pentane converted.

As can be seen, Table 3A and Table 3B show nearly 80% conversion of pentane, at high WHSV, at temperatures 550-600° C. on ZSM-5/1.0% Pt catalysts with 0.2 and 0.02% Na respectively. Selectivity to cyclic $C_5$'s is low, as compared to the performance evaluation in Example 2, while selectivities to cracked products are similar. Selectivity to isomerized $C_5$ products is markedly higher on these low-Na containing catalysts, pointing towards the need for Brønsted acid site titration with sodium or other Group I or Group II metal compounds.

FIGS. 3A and 3B show cyclic $C_5$ yield at varying temperatures, before and after $H_2$ stripping for 0.5 g ZSM-5 (400:1)/0.5% Pt at conditions of 5.0 psia (35 kPa-a) $C_5H_{12}$, 1:1 molar $H_2$:$C_5$, 14.7 WHSV, 45 psia total (310 kPa-a).

In comparison, a catalyst composition of Pt/Sn-ZSM-5 exhibited a 36% conversion of n-pentane with 23% selectivity to cyclic $C_5$ species on a fresh catalyst composition, with a selectivity to cyclic products greatly reduced after $H_2$ stripping at 650° C., demonstrating undesired catalyst composition aging, as noted above.

Example 5—Zeolite Synthesis ($SiO_2$/$Al_2O_3$ Molar Ratio of ~50/1)

A synthesis mixture with a molar Si/A12 ratio of ~60/1 was prepared from DI water, 50% NaOH solution, 43% Sodium Aluminate solution, Tetra-propyl ammonium Bromide solution, ZSM-5 seed crystals, and Ultrasil PM™ Modified silica. These components were mixed in a 5-pail container and then charged into a 5-gal autoclave after mixing.

TABLE 3A

| Temperature | Conversion (%) | Selectivity (C %) | | | | | Yield (C %) | | | | | |
|---|---|---|---|---|---|---|---|---|---|---|---|---|
| (° C.) | $C_5H_{12}$ | $cC_5$ | CPD | $C_1$ | $C_{2-4}$ | $iC_5$ | $cC_5$ | CPD | $C_1$ | $C_{2-4}$ | $iC_5$ | $cC5$:$C_{1-4}$ |
| 550 | 77 | 25 | 14 | 1.4 | 11 | 34 | 19 | 11 | 1.1 | 8.6 | 26 | 1.9 |
| 575 | 78 | 33 | 23 | 1.3 | 9.1 | 22 | 26 | 18 | 1.0 | 7.1 | 17 | 3.2 |
| 600 | 82 | 40 | 31 | 1.2 | 8.1 | 11 | 33 | 25 | 1.0 | 6.6 | 9.0 | 4.3 |
| 600, Post $H_2$ | 79 | 49 | 37 | 1.2 | 7.7 | 7.2 | 39 | 29 | 0.9 | 6.1 | 5.7 | 5.5 |

TABLE 3B

| Temperature | Conversion (%) | Selectivity (C %) | | | | | Yield (C %) | | | | | |
|---|---|---|---|---|---|---|---|---|---|---|---|---|
| (° C.) | $C_5H_{12}$ | $cC_5$ | CPD | $C_1$ | $C_{2-4}$ | $iC_5$ | $cC_5$ | CPD | $C_1$ | $C_{2-4}$ | $iC_5$ | $cC5$:$C_{1-4}$ |
| 550 | 81 | 11 | 7.6 | 0.8 | 15 | 47 | 8.8 | 6.1 | 0.7 | 12 | 38 | 0.7 |
| 575 | 79 | 16 | 13 | 0.8 | 5.7 | 45 | 13 | 10 | 0.6 | 4.5 | 36 | 2.5 |
| 600 | 74 | 19 | 16 | 0.9 | 6.6 | 33 | 14 | 12 | 0.7 | 4.8 | 24 | 2.5 |
| 600, Post $H_2$ | 77 | 28 | 24 | 0.6 | 5.8 | 34 | 22 | 18 | 0.5 | 4.5 | 26 | 4.3 |

Table 3A and Table 3B show the conversion of n-pentane and selectivity/yield of cyclic $C_5$'s, CPD, $C_1$, and $C_{2-4}$ cracking products and isomerized $C_5$'s at varying temperatures (average values over 8 hours at each temperature). 0.5

The mixture was mixed and reacted at 230° F. (110° C.) at 350 rpm for 72 hours. The resulting reaction slurry was discharged and stored in a 5-gal pail container. The XRD pattern (not shown) of the as-synthesized material shows the typical pure phase of ZSM-5 topology. The SEM (not shown) of the as-synthesized material shows that the material was composed of a mixture of small crystals with a size of <0.05 micron. The resulting ZSM-5 crystals had a $SiO_2/Al_2O_3$ molar ratio of ~50/1, Na % of ~0.6 wt %, total surface area (SA)/(micropore SA+mesopore SA) of 475 (393+82) $m^2/g$.

Example 6—ZSM-5(50:1)/1.052% Pt Catalyst Composition Performance Evaluation

The above material of Example 5 was calcined for 6 hours in nitrogen at 900° F. (482° C.). After cooling, the sample was impregnated via incipient wetness with an aqueous solution of sodium nitrate to a sodium level of 1.47 wt % as measured by inductively coupled plasma (ICP). The sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F. (540° C.), the oxygen content was increased to 16.8%, and the material was held at 1000° F. (540° C.) for 6 hours. After cooling, 1.052 wt % Pt as measured by X-ray fluorescence (XRF) was added via incipient wetness impregnation using an aqueous solution of tetraamine platinum hydroxide. The catalyst was dried in air at room temperature then at 250° F. (120° C.), and calcined in air for one hour at 610° F. (320° C.).

The catalyst composition was then tested for performance with feed of n-pentane, $H_2$, and balance He, typically at 550-600° C., 5.0 psia (35 kPa-a) $C_5H_{12}$, 1.0 molar $H_2:C_5H_{12}$, 14.7 $hr^{-1}$ WHSV, and 30 psig (207 kPa) total.

TABLE 4

| Temperature | Conversion (%) | Selectivity (C %) | | | | | Yield (C %) | | | | | |
|---|---|---|---|---|---|---|---|---|---|---|---|---|
| (° C.) | $C_5H_{12}$ | $cC_5$ | CPD | $C_1$ | $C_{2-4}$ | $iC_5$ | $cC_5$ | CPD | $C_1$ | $C_{2-4}$ | $iC_5$ | $cC_5:C_{1-4}$ |
| 550 | 65 | 31 | 19 | 1.3 | 7.4 | 25 | 20 | 12 | 0.9 | 5.0 | 13 | 3.4 |
| 575 | 62 | 45 | 32 | 1.3 | 7.1 | 9.4 | 28 | 19 | 0.8 | 4.4 | 4.9 | 5.3 |
| 600 | 58 | 52 | 41 | 1.5 | 8.0 | 3.8 | 30 | 24 | 0.9 | 4.6 | 1.7 | 5.5 |
| 600, Post $H_2$ | 45 | 48 | 39 | 1.1 | 6.4 | 2.2 | 23 | 18 | 0.5 | 3.0 | 0.7 | 6.4 |

Examples 2 and 6 demonstrate the capability of Pt on MFI aluminosilicates over a broad Si:Al range to perform the conversion of acyclic $C_5$'s to cyclic $C_5$'s with favorable selectivity and stability.

Example 7—Zeolite Synthesis ($SiO_2/Al_2O_3$ Molar Ratio of ~498/1)

A mixture with ~22% solids was prepared from 8,800 g of DI water, 600 g of 50% NaOH solution, 26 g of 43% Sodium Aluminate solution, 730 g of n-propyl amine 100% solution, 40 g of ZSM-5 seed crystals, and 3,190 g of Ultrasil PM™ Modified silica were mixed in a 5-gal pail container and then charged into a 5-gal autoclave after mixing. The mixture had the following molar composition:

| | |
|---|---|
| $SiO_2/Al_2O_3$ | ~470 |
| $H_2O/SiO_2$ | ~12.1 |
| $OH/SiO_2$ | ~0.16 |

-continued

| | |
|---|---|
| $Na/SiO_2$ | ~0.16 |
| n-PA/Si | ~0.25. |

The mixture was mixed and reacted at 230° F. (110° C.) at 350 rpm for 48 hours. The resulting reaction slurry was discharged and stored in a 5-gal pail container. The XRD pattern (not shown) of the as-synthesized material showed the typical pure phase of ZSM-5 topology. The SEM (not shown) of the as-synthesized material showed that the material was composed of mixture of large crystals with size of ~1-2 micron. The resulting ZSM-5 crystals had a $SiO_2/Al_2O_3$ molar ratio of ~498, Na % of ~0.37 wt %, total surface area (SA)/(micropore SA+mesopore SA) of 468 (422+45) $m^2/g$.

Example 8—ZSM-5(498:1) Catalyst Composition Performance Evaluation with Varying Platinum Content The above material of Example 7 was used to form four catalyst compositions having varying platinum content in accordance with the following procedure. First, they calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F. (540° C.), the oxygen content was increased to 16.8%, and the material was held at 1000° F. (540° C.) for 6 hours. After cooling, the desired platinum loading (0.5 wt % in the first composition, 0.2 wt % in the second composition, 0.1 wt %, in the third composition, and 0.06 wt % in the fourth composition) as measured by ICP was added via incipient wetness impregnation using an aqueous solution of tetraamine platinum hydroxide. The catalyst was dried in air at room temperature then at 250° F. (120° C.), and calcined in air for three hours at 660° F. (350° C.).

The catalyst composition was then tested for performance with feed of n-pentane, $H_2$, and balance He, typically at 575° C., 5.0 psia (35 kPa-a) $C_5H_{12}$, 1.0 molar $H_2:C_5H_{12}$, 14.7 $hr^{-1}$ WHSV, and 30 psig (207 kPa) total. Performance results are shown in Table 5 which also includes "STY cC5" values which are calculated site time yield values (i.e., mols of cC5/mol of Pt/second).

TABLE 5

| Catalyst | Conversion (%) $C_5H_{12}$ | Selectivity (C %) | | | | | Yield (C %) | | | | | | STY |
|---|---|---|---|---|---|---|---|---|---|---|---|---|---|
| | | $cC_5$ | CPD | $C_1$ | $C_{2-4}$ | $iC_5$ | $cC_5$ | CPD | $C_1$ | $C_{2-4}$ | $iC_5$ | $cC_5:C_{1-4}$ | $cC_5$ |
| 0.5% Pt | 85 | 46 | 31 | 3.4 | 20 | 4.5 | 39 | 26 | 2.9 | 17 | 2.9 | 2.0 | 0.9 |
| 0.2% Pt | 73 | 42 | 29 | 1.4 | 11 | 3.0 | 31 | 21 | 1.1 | 8.0 | 1.6 | 3.4 | 1.7 |
| 0.1% Pt | 64 | 31 | 22 | 0.8 | 6.6 | 2.0 | 20 | 14 | 0.5 | 4.3 | 0.8 | 4.1 | 2.2 |
| 0.06% Pt | 45 | 20 | 16 | 0.5 | 4.4 | 1.6 | 9.2 | 7.4 | 0.2 | 2.0 | 0.2 | 4.1 | 1.8 |

Example 8 demonstrates the capability of Pt on MFI aluminosilicates over a broad Pt loading range to perform the conversion of acyclic $C_5$'s to cyclic $C_5$'s with favorable selectivity. The STY values demonstrate that efficiency of Pt increases as the loading decreases. This trend appears not to hold for the lowest Pt loading, but that is due to the sequential nature of the reaction (i.e., dehydrogenation followed by cyclization) and insufficient quantity of catalyst in the reactor at very low Pt loadings. Very low Pt loaded catalyst can still be utilized, but would need to be operated at lower WHSV.

Certain embodiments and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values take into account experimental error and variations that would be expected by a person having ordinary skill in the art.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, a process, a method of making, or an element or a group of elements is preceded with the transitional phrase "comprising," it is understood that we also contemplate the same composition, a process, a method of making, or an element or a group of elements with transitional phrases "consisting essentially of," "consisting of," "selected from the group consisting of," or "is" preceding the recitation of said composition, a process, a method of making, or an element or a group of elements, and vice versa.

What is claimed is:

1. A process for conversion of an acyclic $C_5$ feedstock to a product comprising cyclic $C_5$ compounds, said process comprising the steps of contacting said feedstock and, optionally, hydrogen under acyclic $C_5$ conversion conditions in the presence of a catalyst composition to form said product, wherein said catalyst composition comprises a microporous crystalline aluminosilicate selected from the group consisting of ZSM-5, ZSM-11, ZSM-22, ZSM-23, ZSM-35, ZSM-48, ZSM-50, ZSM-57, ZSM-58, a MCM-22 family material, and mixtures of two or more thereof, a Group 10 metal, in combination with a Group 1 alkali metal and/or a Group 2 alkaline earth metal and, optionally, a Group 11 metal.

2. The process of claim 1, wherein said catalyst composition has Group 10 metal content in the range from 0.005 wt % to 10 wt %, based on the weight of the catalyst composition.

3. The process of claim 1, wherein said Group 10 metal is platinum, and said Group 11 metal is copper or silver.

4. The process of claim 1, wherein said Group 1 alkali metal and/or said Group 2 alkaline earth metal is present as an oxide.

5. The process of claim 1, wherein said Group 1 alkali metal is selected from the group consisting of lithium, sodium, potassium, rubidium, cesium, and mixtures of two or more thereof, and/or said Group 2 alkaline earth metal is selected from the group consisting of beryllium, magnesium, calcium, strontium, barium, and mixtures of two or more thereof.

6. The process of claim 1, wherein said microporous crystalline aluminosilicate has a constraint index in the range of 3 to 12.

7. The process of claim 1, wherein said microporous crystalline aluminosilicate has a $SiO_2/Al_2O_3$ molar ratio greater than 25.

8. The process of claim 1, wherein said catalyst composition has an Alpha Value (as measured prior to the addition of the Group 10 metal, and/or prior to the addition of the optional Group 11 metal) of less than 25.

9. The process of claim 1, wherein the molar ratio of said Group 1 alkali metal to Al is at least 1, and/or the molar ratio of said Group 2 alkaline earth metal to Al is at least 1.

10. The process of claim 1, wherein said catalyst composition provides a conversion of at least 70% of said acyclic $C_5$ feedstock under acyclic $C_5$ conversion conditions including an n-pentane feedstock with equimolar $H_2$, a temperature in the range of 550° C. to 600° C., an n-pentane partial pressure between 3 psia and 30 psia at the reactor inlet (21 to 207 kPa-a), and an n-pentane weight hourly space velocity between 5 hr$^{-1}$ and 20 hr$^{-1}$.

11. The process of claim 1, wherein said catalyst composition provides a carbon selectivity to cyclic $C_5$ compounds of at least 30% under acyclic $C_5$ conversion conditions including an n-pentane feedstock with equimolar $H_2$, a temperature in the range of 550° C. to 600° C., an n-pentane partial pressure between 3 psia and 30 psia at the reactor inlet (21 to 207 kPa-a), and an n-pentane weight hourly space velocity between 5 hr$^{-1}$ and 20 hr$^{-1}$.

12. The process of claim 1, wherein said acyclic $C_5$ feedstock comprises pentane, pentene, pentadiene, and mixtures of two or more thereof.

13. The process of claim 1, wherein said cyclic $C_5$ compounds comprise cyclopentane, cyclopentene, cyclopentadiene, and mixtures of two or more thereof.

14. The process of claim 1, wherein said acyclic $C_5$ feedstock comprises at least 75 wt % n-pentane.

15. The process of claim 1, wherein said cyclic $C_5$ compounds comprise at least 20 wt % cyclopentadiene.

16. The process of claim 1, wherein said acyclic $C_5$ conversion conditions include at least a temperature of 450° C. to 650° C., the molar ratio of said optional hydrogen co-feed to the acyclic $C_5$ feedstock is in the range of 0.01 to 3, said acyclic $C_5$ feedstock has a partial pressure in the range of 3 psia to 100 psia at the reactor inlet (21 to 689 kPa-a), and said acyclic $C_5$ feedstock has a weight hourly space velocity in the range from 1 $hr^{-1}$ to 50 $hr^{-1}$.

17. A process for conversion of an acyclic $C_5$ feedstock to a product comprising cyclic $C_5$ compounds, said process comprising the steps of contacting said feedstock and, optionally, hydrogen under acyclic $C_5$ conversion conditions in the presence of a catalyst composition to form said product, wherein said catalyst composition is made by the method comprising the steps of:

(a) providing a microporous crystalline aluminosilicate selected from the group consisting of ZSM-5, ZSM-11, ZSM-22, ZSM-23, ZSM-35, ZSM-48, ZSM-50, ZSM-57, ZSM-58, a MCM-22 family material, and mixtures of two or more thereof comprising a Group 1 alkali metal and/or a Group 2 alkaline earth metal and a constraint index in the range of 3 to 12;

(b) heating said microporous crystalline aluminosilicate in one or more steps to a first temperature of 450° C. or above in an atmosphere which comprises an inert gas;

(c) adding oxygen to said atmosphere until the oxygen concentration in said atmosphere is up to 20% and then cooling said microporous crystalline aluminosilicate; and (d) contacting said cooled microporous crystalline aluminosilicate of step (c) with a source of a Group 10 metal, optionally a source of a Group 11 metal, to form said catalyst composition, whereby said catalyst composition has said Group 10 metal, and/or said optional Group 11 metal, deposited thereon.

18. The process of claim 17, wherein said Group 10 metal is platinum and said source of platinum is selected from the group consisting of platinum nitrate, chloroplatinic acid, platinous chloride, platinum amine compounds, tetraamine platinum hydroxide, and mixtures of two or more thereof, and/or said optional Group 11 metal is copper and said source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof, and/or said Group 11 metal is silver, and/or said source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof.

* * * * *